United States Patent
Cedro, Jr. et al.

(10) Patent No.: US 10,194,897 B2
(45) Date of Patent: Feb. 5, 2019

(54) MECHANICAL RETRACTION VIA TETHERING FOR LUNG VOLUME REDUCTION

(71) Applicant: Ethicon, Inc., Somerville, NJ (US)

(72) Inventors: Rudolph Cedro, Jr., Clinton, NJ (US); Daniel J. Smith, Dayton, NJ (US)

(73) Assignee: Ethicon, Inc., Somerville, NJ (US)

( * ) Notice: Subject to any disclaimer, the term of this patent is extended or adjusted under 35 U.S.C. 154(b) by 62 days.

(21) Appl. No.: 14/795,268

(22) Filed: Jul. 9, 2015

(65) Prior Publication Data

US 2016/0015377 A1    Jan. 21, 2016

Related U.S. Application Data

(60) Provisional application No. 62/026,299, filed on Jul. 18, 2014.

(51) Int. Cl.
*A61B 17/04* (2006.01)
*A61B 17/12* (2006.01)
*A61B 17/00* (2006.01)

(52) U.S. Cl.
CPC .... *A61B 17/0401* (2013.01); *A61B 17/12104* (2013.01); *A61B 17/12172* (2013.01); *A61B 2017/00809* (2013.01); *A61B 2017/00867* (2013.01); *A61B 2017/00889* (2013.01); *A61B 2017/00893* (2013.01); *A61B 2017/0409* (2013.01); *A61B 2017/0412* (2013.01); *A61B 2017/0414* (2013.01);
(Continued)

(58) Field of Classification Search
CPC ........ A61B 17/12172; A61B 17/12104; A61B 2017/00809; A61B 2017/00867; A61B 2017/0448; A61B 2017/0451; A61B 2017/0496; A61B 2017/00893; A61B 2017/0446; A61B 2017/0458; A61B 2017/0445; A61B 2017/0414; A61B 2017/0412; A61B 2017/0409; A61B 2017/00889

See application file for complete search history.

(56) References Cited

U.S. PATENT DOCUMENTS

| | | |
|---|---|---|
| 5,507,754 A | 4/1996 | Green et al. |
| 6,080,182 A | 6/2000 | Shaw et al. |

(Continued)

FOREIGN PATENT DOCUMENTS

| | | |
|---|---|---|
| WO | WO 2001/066190 | 9/2001 |
| WO | WO 2013/003632 | 1/2013 |
| WO | WO 2013/028579 | 2/2013 |

OTHER PUBLICATIONS

Gompelmann D., et al. 'Predicting Atelectasis by Assessment of Collateral Ventilation prior to Endobronchial Lung Volume Reduction: A Feasibility Study.' Respiration. (2010) 80(5) pp. 419-425.

(Continued)

*Primary Examiner* — Richard Louis
(74) *Attorney, Agent, or Firm* — Frost Brown Todd LLC

(57) ABSTRACT

A device and method for reducing the volume of a tissue region, the device including a first fixation element, a second fixation element, and a tethering device, where the first and second fixation elements are slidably secured onto said tether, and the first and second fixation elements are radially self-expanding fixation elements.

20 Claims, 8 Drawing Sheets

(52) U.S. Cl.
CPC ........... *A61B 2017/0445* (2013.01); *A61B 2017/0446* (2013.01); *A61B 2017/0448* (2013.01); *A61B 2017/0451* (2013.01); *A61B 2017/0458* (2013.01); *A61B 2017/0496* (2013.01)

(56) References Cited

U.S. PATENT DOCUMENTS

| | | |
|---|---|---|
| 6,174,323 B1 | 1/2001 | Biggs et al. |
| 6,514,290 B1 | 2/2003 | Loomas |
| 6,599,311 B1 | 7/2003 | Biggs et al. |
| 6,997,189 B2 | 2/2006 | Biggs et al. |
| 7,434,578 B2 | 10/2008 | Dillard et al. |
| 7,757,692 B2 | 7/2010 | Alferness et al. |
| 8,142,455 B2 | 3/2012 | Thompson et al. |
| 8,157,823 B2 | 4/2012 | Aronson et al. |
| 8,157,837 B2 | 4/2012 | Thompson et al. |
| 8,186,355 B2 | 5/2012 | van der Burg et al. |
| 8,282,660 B2 | 10/2012 | Thompson et al. |
| 8,323,202 B2 | 12/2012 | Roschak et al. |
| 8,632,605 B2 | 1/2014 | Thompson et al. |
| 2002/0183787 A1* | 12/2002 | Wahr ............... A61B 17/0057 606/213 |
| 2004/0078054 A1 | 4/2004 | Biggs et al. |
| 2004/0143282 A1 | 7/2004 | Dillard et al. |
| 2005/0043759 A1* | 2/2005 | Chanduszko ...... A61B 17/0057 606/213 |
| 2005/0251209 A1* | 11/2005 | Saadat ............. A61B 17/0401 606/232 |
| 2005/0277966 A1* | 12/2005 | Ewers ............. A61B 17/0401 606/153 |
| 2006/0217762 A1* | 9/2006 | Maahs ............. A61B 17/0401 606/213 |
| 2007/0233188 A1* | 10/2007 | Hunt ............... A61B 17/00234 606/228 |
| 2008/0119891 A1* | 5/2008 | Miles ............... A61B 17/0057 606/213 |
| 2008/0215072 A1 | 9/2008 | Kelly |
| 2008/0215086 A1* | 9/2008 | Olsen ............... A61B 17/0057 606/213 |
| 2009/0318956 A1* | 12/2009 | Belef ............... A61B 17/0057 606/213 |
| 2013/0184579 A1 | 7/2013 | Roschak et al. |

OTHER PUBLICATIONS

Herth FJ, Eberhard R, Gompelmann D.Slebos DJ.Ernst A.. Bronchoscopic lung volume reduction with a dedicated coil: a clinical pilot study. Ther Adv Respir Dis. 2010;4(4):225-231.
Sciurba F.C. et al;. 'A Randomized Study of Endobronchial Valves for Advanced Emphysema.' N Engl J Med. (2010) 363(13) pp. 1233-1244.
Wood D.E. et al. 'A multicenter trial of an intrabronchial valve for treatment of severe emphysema.' J Thorac Cardiovasc Surg. (2007) 133(1) pp. 65-73.
International Search Report re: PCT/US2015/039705 dated Sep. 23, 2015.
International Search Report re: PCT/US2015/039708 dated Oct. 27, 2015.
Written Opinion re: PCT/US2015/039705 dated Sep. 23, 2015.
Written Opinion re: PCT/US2015/039708 dated Oct. 27, 2015.
U.S. Appl. No. 14/795,268, filed Jul. 9, 2015.
European Examination Report dated May 22, 2018 for Application No. EP 15747270.5, 5 pgs.
U.S. Appl. No. 62/026,299, filed Jul. 18, 2014.

* cited by examiner

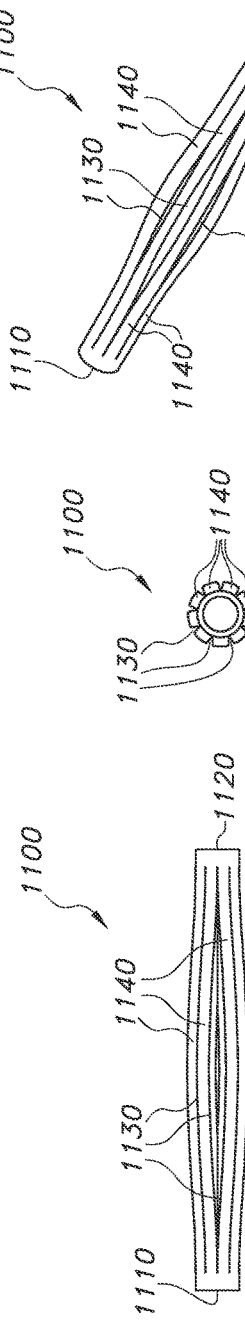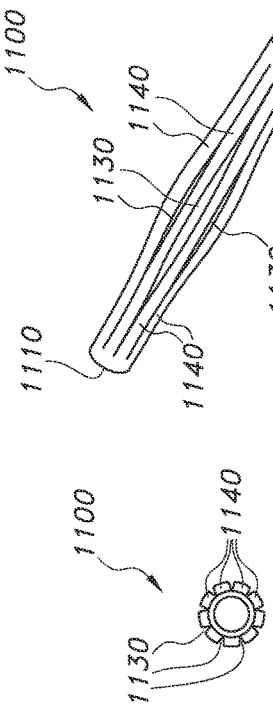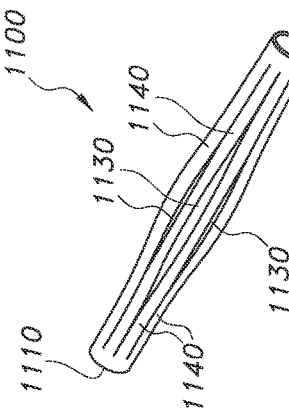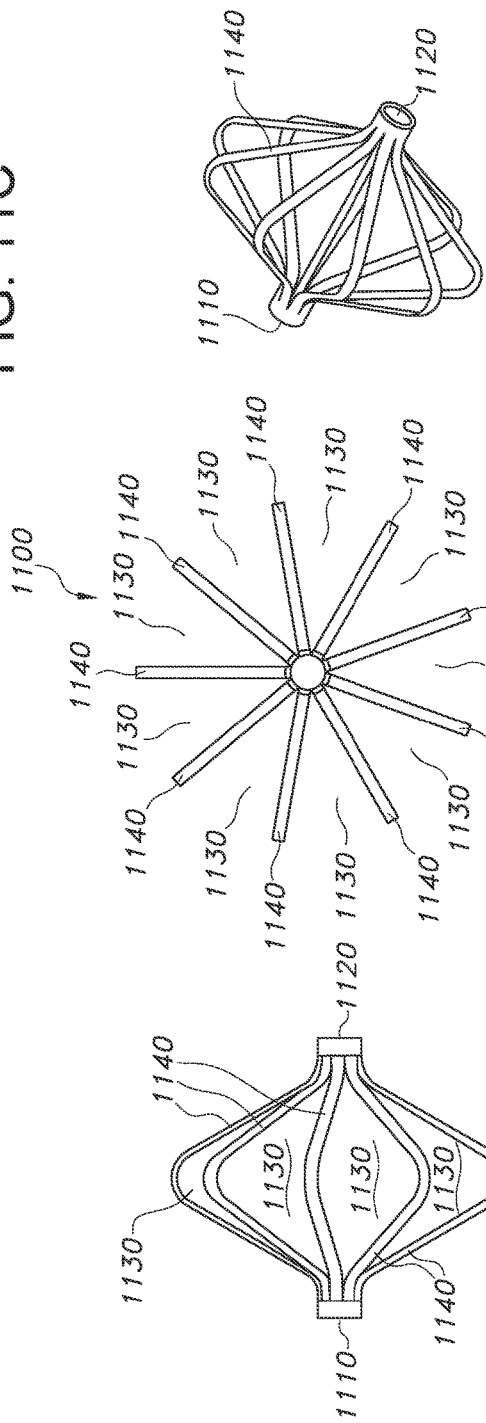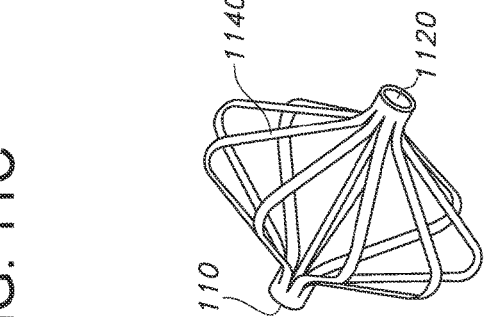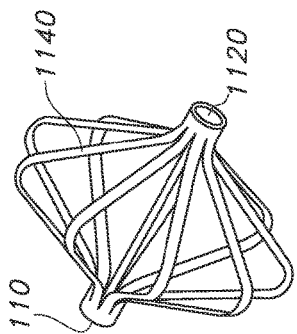

MECHANICAL RETRACTION VIA TETHERING FOR LUNG VOLUME REDUCTION

CROSS-REFERENCE TO RELATED APPLICATIONS

The present invention claims priority to U.S. Provisional Application No. 62/026,299, filed on Jul. 18, 2014, the entire contents of which are incorporated by reference herein.

FIELD OF THE INVENTION

The present invention relates to mechanical methods of reducing lung volume. The invention includes an implantable device and method of implanting the device to provide tethering and reduction of the volume.

BACKGROUND

In a deceased lung, having COPD or emphysema, patients have trouble getting proper oxygen transfer which results in shortness of breath and major impact on their quality of life. To help improve the quality of life in such individuals, thoracic surgery to remove a portion of the lung has been a leading method of choice. However, such methods are drastic measures and have been associated with increased clinical issues including morbidity. Less invasive means of lung volume reduction (LVR) have been attempted, such as implantation of valves, coils, or sealants. These interventional treatments to LVR (ILVR) have varying degrees of affectivity and associated complications but are better tolerated by these very ill patients.

One previous attempt includes that described in U.S. Pat. No. 6,174,323, which uses two piercing anchors to be provided in different lung regions, where the two piercing anchors are connected to a tethering device. After implantation of the two piercing anchors, the tethering device is pulled, which pulls both anchors towards the tethering device. Previous attempts such as these, however, do not provide reversible and retrievable devices and methods, and they can be highly invasive as well as destructive to the airway causing tearing and puncturing which leads to bleeding and tissue trauma. Thus, a goal of the present invention is to provide a highly effective means of ILVR which can be implemented quickly and safely, and be reversible and possibly retrievable if needed. It is also useful to provide a device that is not highly invasive or destructive to the airway, and which has a lower likelihood of tearing or puncturing, and which does not or minimizes bleeding and tissue trauma.

SUMMARY

In one aspect of the present invention, there is provided a tissue retraction device. The device may include at least two fixation elements, desirably atraumatic fixation elements, the fixation elements connected by at least one tether. Each fixation element in one aspect is a radially expandable device, which may include a tubular configuration when compressed, but in expanded state the first and second ends of the tube move toward each other and the central region of the tube expands radially to form struts. The struts may be formed from forming a plurality of slits or windows in the outer circumference of the tubular structure. The diameter (as measured at its central region) is from about 2 to about 20 times the diameter of the compressed tubular structure. Methods of making and using these devices are also described herein.

BRIEF DESCRIPTION OF THE FIGURES

FIGS. 8A-1 and 8A-2 show a locking mechanism prior to locking FIGS. 8B-1 and 8B-2 show a locking mechanism after locking.

FIGS. 11A-11C show a fixation element in collapsed state.

FIGS. 12A-12C show the fixation element of FIGS. 11A-11C in expanded state.

DETAILED DESCRIPTION

Figure 1:
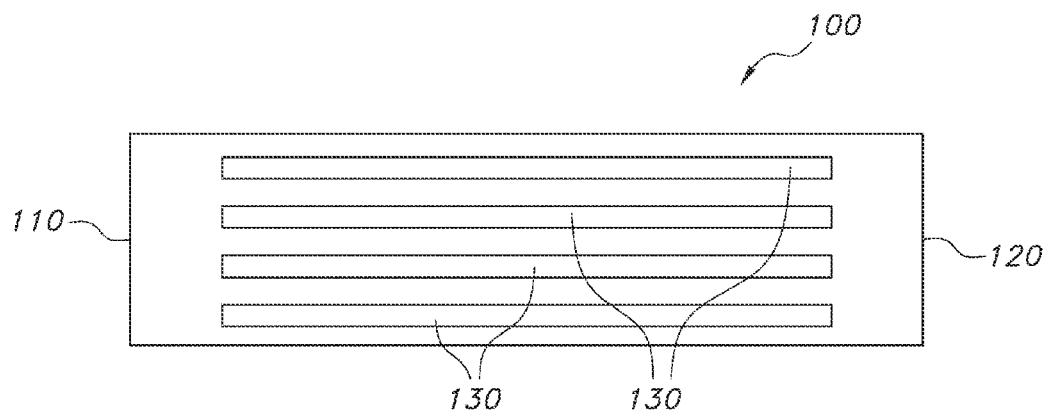
FIG. 1 shows a side view of a fixation element useful in the present invention prior to expansion.

The present invention relates to a mechanical device suitable for implantation into a subject, the subject may be a mammal, such as a human. The device may be implanted into any tissue region where desired, including, for example, soft tissue locations such as in the lung, liver, brain, or any soft tissue location. In particular, the device is suitable for implantation into a lung of the subject. The invention includes the implantable device, alone or as part of a system, and also includes methods of implanting the device to the target site. The implantation of the device includes the use of at least one radially expandable fixation element, similar to the anchors in prior attempts discussed above, however, radially expandable fixation elements in the present invention are capable of providing holding strength while also being easily removable and moved if such removing is required. As used herein, the term "fixation element" is understood to refer to an expandable fixation element, which is better understood through the description below and Figures.

The device is useful in that it can be removably implanted into the lung or other body region of a user, allowing for one or both fixation elements to be compressed and removed without damage to the tissue of the individual in which the device is implanted. Further, as will be described below, the device is implanted by first releasing one fixation element into a target site, then manipulating the tissue into which the fixation element is implanted, and releasing a second fixation element. The second fixation element is then locked into place to secure the device. There may be one further step of pulling one or more fixation elements after both fixation elements are implanted to achieve a desired locked tethering effect, if desired.

The device includes a biocompatible tether, such as a suture or other flexible elongated device, with at least one fixation element at a first end and at least a second fixation element at a second end. The fixation elements are made of a biocompatible material, desirably a material that can provide self-expanding properties, such as nitinol. The fixation elements are generally tubular in shape, with an open central interior extending along its central axis. Each end (a first and second end) is open, such that the length of tether material can be fed through the fixation element completely (extending from the first end, through the fixation element, exiting the second end). The device is delivered such that the first fixation element is delivered at a distal end (distal being furthest away from the user delivering the device), and a second fixation element is delivered at a proximal end (proximal being closest to a user delivering the device).

The fixation element is compressible to a first configuration and expandable to a second configuration. The second configuration (the expanded state) is the configuration in which the fixation element takes when no external forces are acted thereon. The first configuration is achieved when the fixation element is compressed into a tubular shape, which may have any cross sectional configuration, including, for example, circular, square, triangular, diamond, and other shapes. Along the outer circumference of the tubular shape is a plurality of slits, or alternatively a plurality of windows. The slits or windows in the device can be made by a variety of mechanical, laser, energy, and/or chemical means.

FIG. 1 shows a side view of one fixation element suitable in the present invention. The fixation element 100 includes a first end 110 and second end 120, with an intervening length therebetween. The first end 110 and second end 120 may be free of slits, and in such embodiments may be considered a slit-free first end 110 or a slit-free second end 120. When compressed, an fixation element may have a length of from about 1/8 inch to about 2 inches, and desirably between about 1/4 inch and about 1 inch, more desirably about 3/8 inch to about 3/4 inch. The fixation element 100 is tubular, with an open axial center (not seen), and each end (first end 110, second end 120) has an open region extending into the open axial center. Along the sidewalls of the fixation element 100 is a plurality of elongated slits 130. The number of slits 130 may vary, and may include as few as about 2 to about 4 slits, or as many as about 40 to about 50 slits, depending upon the intended effect. In some aspects, the device has about 5-30 slits and more desirably about 10-20 slits. The slits extend axially and may span any length of the fixation element 100 wall. The slits 130 may have any width (measured along the circumference of the fixation element 100 tube), such as from about 0.05 mm to about 2 mm. A larger size slit 130, which has a width of from about 1-2 mm may be considered a "window". The figures and description herein will reference these sections as slits, but it is understood that the description applies to windows as well. It is understood that as the number of slits 130 may increase or decrease, and the size of the window could increase or decrease.

The compressed diameter is equal to or slightly larger than the original tube diameter. The expanded diameter is larger than the unexpanded tube diameter, and may generally be at or less than about 20 times the unexpanded tube diameter depending on the application. The axial length of the compressed fixation element may be equal to or slightly shorter than the initial tube length, while the expanded axial length becomes a function of number and size of the slits, as well as the manufacturing parameters and device used to set the fixation element. The initial length and diameter of the fixation element, as well as the final expanded size, shape and configuration may depend upon a number of factors, including the degree of compression upon formation, the temperature at setting, and the shape of the formation machinery used to prepare the device.

The device 100 in a compressed state has an axial length as measured from first end 110 to second end 120. When expanded, as noted above, the axial length becomes smaller due to the radial expansion of the struts. In an expanded state, the device 100 may have any size axial length (which is determined by the extent of expansion). At its shortest axial length, the expanded device will have an axial length equal to the size of the slit-free first end plus the size of the slit-free second end, plus twice the thickness of the struts. This would envision an expansion whereby the struts are fully pressed against each other and the first and second ends 110, 120 are pulled together as close as possible.

The force exerted by the expanded fixation element once it is in the expanded state may vary depending upon the desired strength of the fixation element. Expanded force will be a function of final wall thickness (pre or post processing), as well as the diameter of the fixation element, and/or the heat set position and temperature at time of use. Additionally expanded force may also be linked to expanded diameter, such that the expanded force will change as the fixation element is expanding and therefore may exert radially outward forces depending on how much it is allowed to expand once deployed. For example, if the fixation element is deployed in a vessel of 4 mm ID, the fixation element may only expand to 6 or 8 mm due to the strength of the vessel wall, even though the free expanded size of the fixation element may be 10 to 12 mm. This feature may provide a valuable and interesting function, such that having an increased outward or radial force as load or expansion continues.

It is also understood that if pulled with sufficient force, the first end 110 could be inverted to touch the second end 120, thus forming a reinforced umbrella like structure having an equal to or smaller maximum free expansion diameter.

Each slit 130 may have any axial length desired. In some embodiments, the slits 130 may have a length of from about 98% of the overall fixation element 100 length to about 30% of the overall fixation element 100 length. Desirably, the slit 130 has a length of from about 70% to about 90% of the overall fixation element 100 length. Between each slit 130 is a length of fixation element material, which connects the first end 110 to the second end 120. The length of fixation element material is referred to as a strut, and each strut may have a width (as measured along the circumference of the fixation element 100) from about 0.1 mm to about 2 mm. Thus, the struts may have a width slightly larger than or equal to the width of the slits 130. The ratio of the width of a strut to a slit is from about 10 to about 1, and more desirably about 3 to about 1. As will be appreciated, the length of the struts will be approximately equal to the length of the slits 130, since the slits 130 form the struts.

Figure 2:
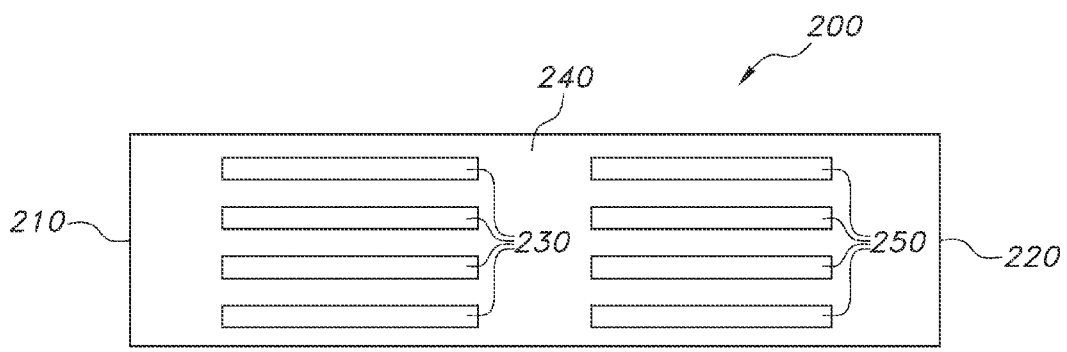
FIG. 2 shows an alternative embodiment of a fixation element prior to expansion.

FIG. 2 shows an embodiment including a plurality of slits axially spaced from each other. The tubular fixation element 200 includes a first end 210 and second end 220, as described above. This fixation element 200 includes a first plurality of axially extending slits 230 at the first end 210 and a second plurality of axially extending slits 250 at the second end 220. Although the Figure shows them as generally equal, it is understood that the lengths 230 and 250 need not be equal in length, and in fact, may alternate in length as well as relative position throughout central region 240. Between the first and second pluralities of axially extending slits (230, 250), there is a tubular central region 240. The tubular central region 240 extends around the entire circumference of the fixation element 200. Axially extending slits 230, 250 may have similar or differing lengths, or they may have staggered lengths and relative positions in the same fixation element 200. For example, first plurality of axially extending slits 230 may be located at a first axial position, while second plurality of axially extending slits 250 may be located at a second axial position, where the first and second axial positions are off-set from each other along the axis of the element 200.

The configurations seen in FIGS. 1 and 2 show the fixation elements 100, 200 in compressed states. As noted above, the compressed state of the fixation element results in a substantially tubular configuration. The fixation elements are self-expanding fixation elements, made from expandable materials, such as nitinol, stainless steel, and polymeric materials, and combinations thereof. In the absence of force thereon, the central region of the fixation element (e.g., between the first end and second end) expands radially outward. Given the radial expansion of the central region, the first end (110, 210) and second end (120, 220) will be moved axially inward toward each other, thus reducing the overall axial length of the fixation element (100, 200).

Figure 3:
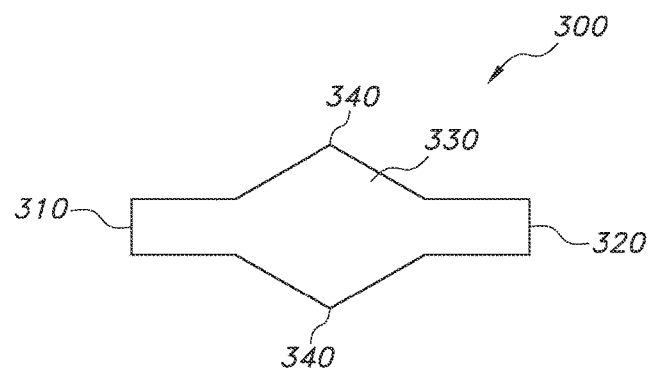
FIG. 3 shows an example of a configuration of an expanded fixation element.

One such expanded configuration can be seen in FIG. 3, which is a side view of an expanded fixation element 300. The fixation element 300 includes a first end 310 and second end 320, and the fixation element 300 has a plurality of axially-extending slits (not seen). In the expanded state, the fixation element 300 has a central region 330 that is expanded radially outward. In some embodiments, the central region 330, when expanded, forms a peak 340, which extends about the circumference of the fixation element 300. The expanded fixation element 300 therefore may have a central region 330 that is substantially diamond-like in cross-section.

Figure 4:
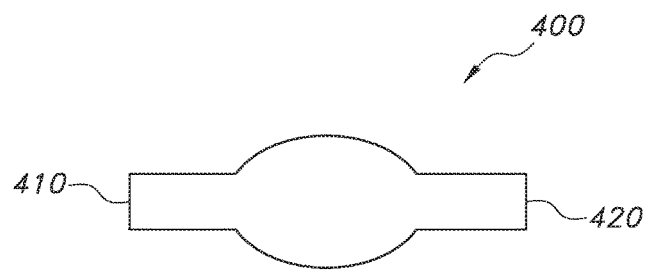
FIG. 4 shows an alternate example of a configuration of an expanded fixation element.

FIG. 4 shows an expanded fixation element 400 that is has a more elliptical, spherical, radial or conical shape. As with FIG. 3, the fixation element of FIG. 4 has a ratio of expanded diameter to length that can vary greatly as described above based on application. The radial shape seen in FIG. 4 may be less traumatic to certain tissues as compared to that seen in FIG. 3, however the fixation element of FIG. 4 may have increased or decreased pull out load as compared to that in FIG. 3. The fixation element 400 includes a first end 410 and second end 420, as described above. Of course, the overall design, including shape, slits, surface roughness, material, and the like may vary as needed or desired to achieve the intended holding strength and fixation.

Figure 5:
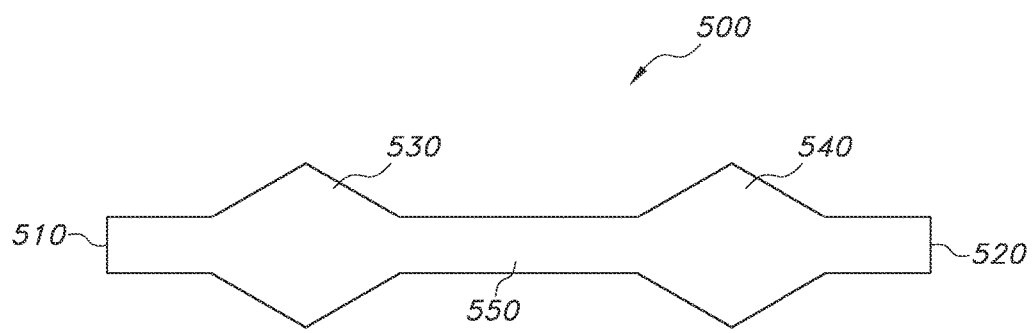
FIG. 5 shows another example of a configuration of an expanded fixation element with multiple expandable regions.

FIG. 5 shows a fixation element that includes a plurality of expandable sections. As can be seen, the fixation element 500 includes a first end 510 and second end 520, with an intervening axial length therebetween as described above. However, this fixation element 500 includes a first expandable section 530 and second expandable section 540, with a non-expandable (or minimally expandable) central region 550 therebetween. Each expandable section (530, 540) is similar to that described above in FIGS. 3 and 4. The first and second expandable sections (530, 530) need not be equal in size, shape, length or symmetry, and need not both be processed in the same way to achieve the same outward radial force.

Figure 6:
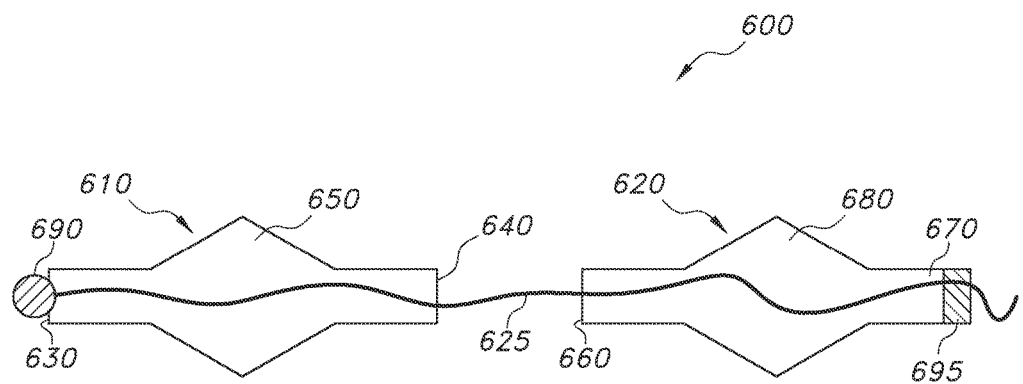
FIG. 6 shows a device with two fixation elements and a tether.
Figure 7:
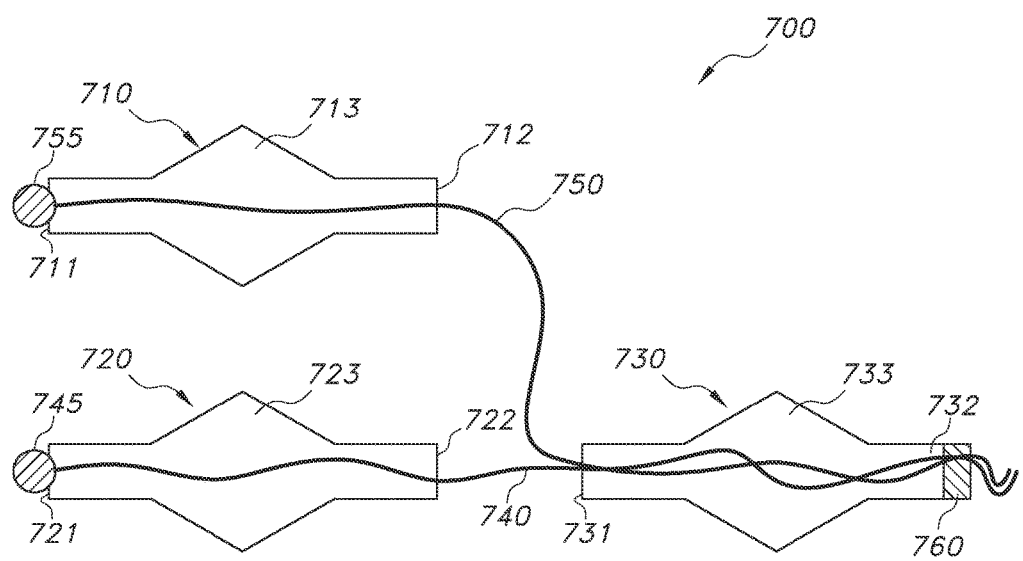
FIG. 7 shows a device with more than two fixation elements and tethers.

FIGS. 6 and 7 show embodiments of tethering devices. FIG. 6 shows a device including two fixation elements, and FIG. 7 shows a device including more than two fixation elements. As seen in FIG. 6, a tethering device 600 includes a first fixation element 610 and second fixation element 620, which are generally tubular in shape (when compressed) and include an open central axis. The device 600 includes a length of flexible cord-like material, such as a tether 625. Each fixation element 610, 620 is placed over the tether 625, such that the tether 625 extends through the axial center of each fixation element 610, 620. First fixation element 610 includes first end 630 and second end 640, and the tether 625 extends from first end 630 to second end 640. The tether 625 may terminate within fixation element 610, 710, or 720, or closer to or at end 640, 712 or 722 respectively, and would still allow the device to function in the same manner. As described above with regard to FIGS. 3 and 4, the first fixation element 610 includes a radially expandable central region 650, which, in the absence of force thereon, expands radially outward. Similarly, second fixation element 620 includes first end 660 and second end 670, and the tether 625 extends from first end 660 to second end 670. As with the first fixation element, the second fixation element 620 includes a radially expandable central region 680, which, in the absence of force thereon, expands radially outward. Tethered devices, as, for example 610 and 680, do not need to be of equal size, diameter, or length and may have different outward radial forces.

The tether 625 may have any configuration or cross-sectional shape or design desired, and may be circular in cross-section, triangular, square, star-shaped, or any other desired cross-section, and it may be made from different material as the fixation element(s). The shape may be configured to fit and hold airways open and facilitate drainage of fluids, if desired. Through the use of a channeled tether 625, fluid can flow through the tether body. If the tether 625 includes a configuration such as diamond, square, or star shaped (for example), there will be regions of the tether body 625 that may not abut the side walls of the tissue into which it is implanted, and therefore fluid may flow outside the tether body 625. It is desired that the diameter of the tether 625 be smaller than any of the open ends of the fixation elements used in the device, so that the fixation elements 610, 620 may be slid along the tether 625. Further, it is desired that there be some open space surrounding the outer circumference of the tether 625 to allow for fluid flow through the fixation element.

The sizes of the two fixation elements 610, 620 may differ. First fixation element 610 may be smaller than the second fixation element 620, for example, or vice versa. That is, first fixation element 610 may have an axial length that is less than that of the second fixation element 620, or first fixation element 620 may have a circumference that is smaller than the circumference of the second fixation element 620 or vice versa. It is desired that the length of tether 625 be greater than the compressed axial length of the first fixation element 610 and the compressed axial length of the second fixation element 620 combined. The tether may be as long as needed to exit the working channel of the deployment device (such as catheter, bronchoscope or other instrument) and have sufficient length for the clinician to apply tension while locating the locking feature 695 before removing a portion of the tether beyond locking feature 695. The amount of retraction applied to contract first fixation element 610 to second fixation element 620 is determined by the clinician, and may range from about 1 mm to about 150 mm, or about 5 mm to about 100 mm, and may be from about 10 mm to about 50 mm as an example of one set of tethered devices.

The fixation elements 610, 620 are slidably movable along the length of the tether 625, given the open axial centers of each fixation element. At the first end of the tether is a termination feature 690, which is secured to the tether 625 and is sized to be larger than the open first end 630 of the first fixation element 610. Thus, termination feature 690 secures the first fixation element 610 onto the tether 625. The termination feature 690 may be secured to the first fixation element 610 such that the first fixation element 610 cannot slide along the length of the tether 625, if desired. 690 can be located beyond or within 610 and can be itself expandable in size or shape once inserted, or of a design as to cam once inserted such that it is larger than opening 630.

The tether includes a locking feature 695 at the second end, which abuts the second end 670 of the second fixation element 620. The locking feature 695 may be any locking feature, including a clamp or other movable object that can be slid or adjusted along the length of the tether 625. When the locking feature 695 is in its locking state, it secures the second fixation element 620 in place with respect to the tether 625. As will be described below, after the first and second fixation elements are implanted in their desired locations, the locking feature 695 may be used (or activated, or applied) to hold the second fixation element 620 in its location on the tether 625, thus holding the device 600 in place. Locking feature 695 does not need to be separate from second fixation element 620, as it can be part of second fixation element 620, as such it can be either built into second fixation element 620, integral to second fixation element 620 or attached to second fixation element 620. One suitable locking feature is depicted in FIG. 8 below.

FIG. 7 shows a device 700 with more than two fixation elements, which may have configurations similar to that in FIG. 3 or 4, described above. In this Figure, three fixation elements are depicted, but more than three fixation elements can be used if desired. In this embodiment, at its first end, the device 700 includes a first fixation element 710, which has a first end 711, second end 712, and radially expandable central region 713. As described above, the first fixation element 710 is generally tubular in shape when compressed, including an open axial central region extending from first end 711 to second end 712. Also at its first end, the device 700 includes a second fixation element 720, which has a first end 721, second end 722, and radially expandable central region 723. As described above, the second fixation element 720 is generally tubular in shape when compressed, including an open axial central region extending from first end 721 to second end 722. At its second end, the device 700 includes a third fixation element 730, which has a first end 731, second end 732, and radially expandable central region 733. As described above, the third fixation element 730 is generally tubular in shape when compressed, including an open axial central region extending from first end 731 to second end 732.

The device 700 includes a plurality of elongated flexible cords, such as tethers, 740 and 750. In this Figure, the tethers 740, 750 are seen as separate elements, but it is contemplated that the tethers may be part of one single tether that is separated to form two separate cords. The first tether 750 is fed through the first fixation element 710, where the fixation element 710 is secured by means of first termination feature 755. The second tether 740 is fed through the second fixation element 720, where the second fixation element 720 is secured by means of a second termination feature 745.

Both the first and second tethers 740, 750 are fed through the open axial center of the third fixation element 730, where each tether 740, 750 may have a locking feature 760 secured thereto. One locking feature 760 may be used to secure both tethers 740, 750 when implanted. The embodiment of FIG. 7 may include more than two fixation elements at the first end of the tethers, with the proviso that for every fixation element (at the first end), there is a tether secured thereto. Each tether may be fed through one fixation element at the second end (e.g., the third fixation element 730), or there may be multiple fixation elements at the second end of the tethers. Device 700 may employ all or none of the featured variations discussed or described above for devices 100, 200, 300, 400, 500 and 600.

As noted above, the fixation elements are slidable axially along the tether, and therefore a suitable locking element is useful in preventing unwanted migration after implantation. Each fixation element in the device may include this locking feature. Specifically, each locking feature should be capable of preventing migration in a first axial direction but allowing migration in the opposite axial direction, to allow implantation and placement but maintain its position after fixation is complete. Alternatively, only one fixation element may be axially movable, while a second fixation element is fixed or cinched at the opposite end of the device (at the opposite end of the tether, for example. A fixation element is therefore capable of sliding along the tether, and locking in desired location to cinch or take-up slack in closure line length, bringing proximal and distal fixation elements closer together, and trapping tissue from the diseased tissue The locking mechanism is operatively incorporated into the fixation element to secure the fixation element to the tether. In one embodiment, described below in FIGS. 8A-8B, the locking member may be an integral part of the fixation element, formed into the hub of the fixation element. In another embodiment of the invention, the locking mechanism may be a functionally separate component or member that, although is physically a separate member, is functionally integrated with the fixation element. That is to say, the locking mechanism can secure to the tether and prevent relative movement between the tether and the fixation element when the hub of the fixation element comes in contact with the locking mechanism. Examples of functionally similar commercial locking mechanisms include the DePuy Mitek RAPIDLOC™ device; zip ties; and similar linear locking devices known in the art.

Figures 1, 8A:
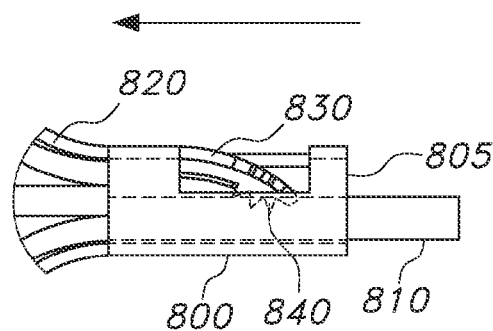
Figures 2, 8A:
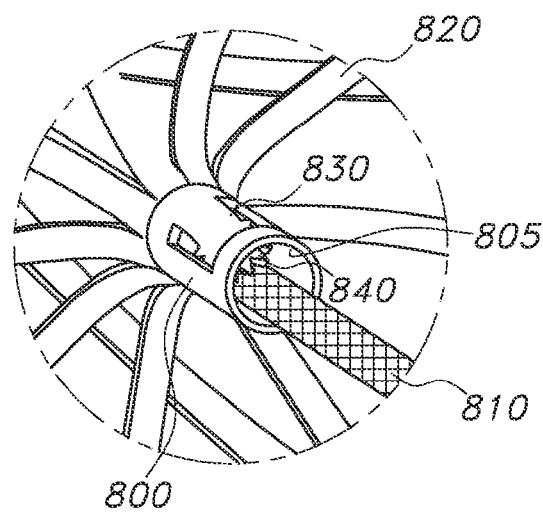
Figures 1, 8B:
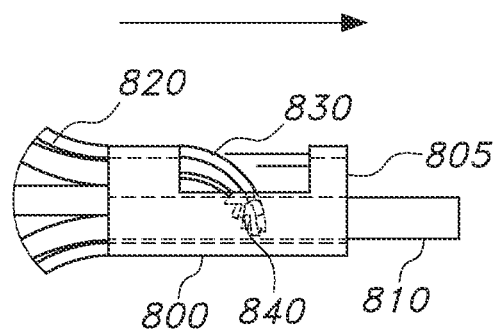
Figures 2, 8B:
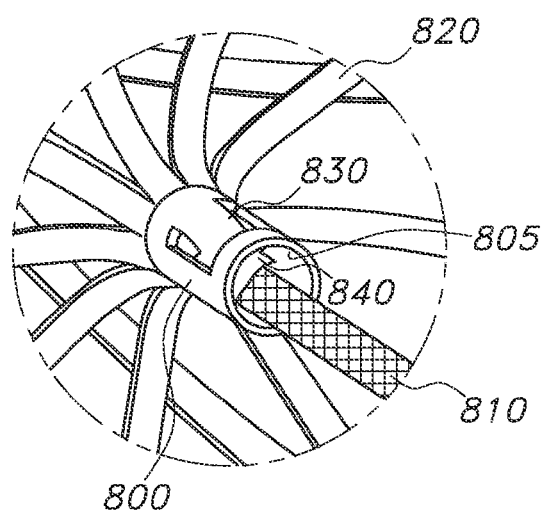
Figure 9:
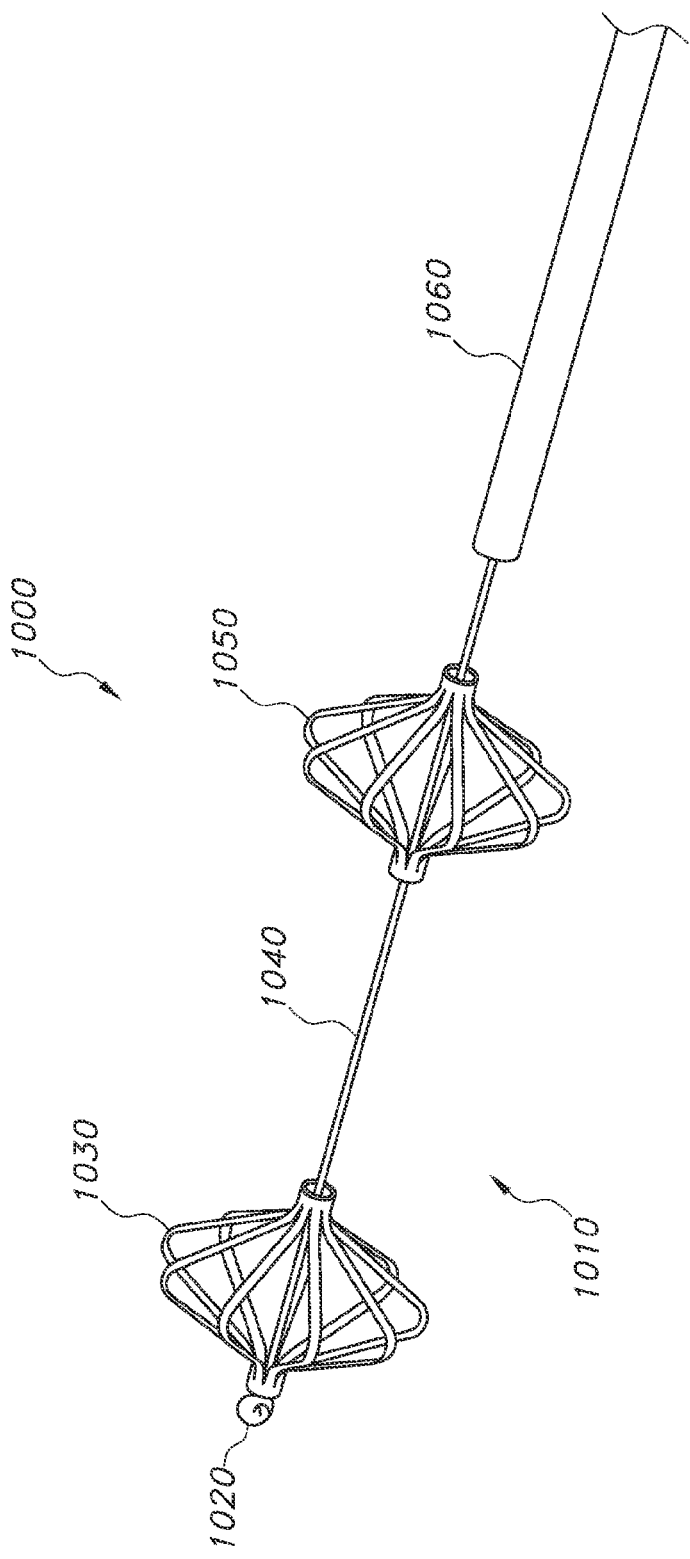
FIG. 9 shows deployment of a device in expanded state.

FIGS. 8A-8B depict a locking element useful in the present invention. FIG. 8A-1 is a side view of a fixation element 800 in an unlocked configuration, and FIG. 8A-2 is a top perspective view of FIG. 8A-1. FIG. 8B-1 is a side view of the fixation element 800 in a locked configuration, while FIG. 8B-2 is a top perspective view of FIG. 8B-2. These figures show one exemplary fixation element 800, which includes a generally tubular region 805 into which a tether 810 may be inserted and held. The fixation element 800 includes a radially expandable region 820, as described above. One suitable locking element includes a tang 830, which includes a depression end 840, in contact with the body of the tether 810. Depression end 840 may include a series of protrusions or teeth to grip the body of the tether 810 and hold it in place against the inside of the tubular region 805. As seen in FIGS. 8A-1 and 8A-2, the tang 830 abuts the tether 810, but does not press against the tether 810, and the tether 810 is free to move axially. When set and in the locking configuration, as seen in FIGS. 8B-1 and 8B-2, the tang 830 is pressed against the body of the tether 810, and specifically the depression end 840 is pressed firmly against the tether 810, pressing the tether 810 against the interior of the tubular region 805. The use of grips or teeth on the depression end 840 may be useful in increasing the holding strength of the tether 810 in its locked position, particularly when the tether is a braided or multifilament device, which includes regions into which the grips or teeth can be inserted. This embodiment of a locking feature may also be used if the tether is a monofilament device, or alternatively the locking feature may vary in design and could be a wedge, friction or torturous path which may compress the tether against an internal side wall of the tubular region 805.

To achieve and maintain the proximity between the proximal and distal fixation elements, it may be necessary to adjust the proximal fixation element by uni-axially cinching or sliding the proximal fixation element along tether. In one embodiment of the invention, cinching comprises uni-axially adjusting the proximal fixation element relative to a tether associated with the closure device. In another embodiment of the invention, cinching comprises incrementally adjusting a first fixation element relative to the tether associated with the closure device. Once the closure device is cinched in place the method may further comprise assessing the degree of proximation between the proximal and distal fixation elements to determine the effect of the cinching to the airway. For example, the clinician may visually assess the proximation though a bronchoscopic or fluoroscopic procedure. In addition, other methods may be used to measure the proximation between the proximal and distal fixation elements to determine airway condition, such as through air exchange as well as fluoroscopic imaging.

After proper cinching, any unwanted length of tether that remains unconstrained within the airway may be mechanically removed. Devices known in the art capable of removing the excess tether include catheter-based snare and cut devices. In addition to independent devices, a mechanical cut and removal mechanism may be integrated into the deployment device.

In use, the device is fed through a delivery catheter, which may have a plurality of internal lumens for delivery of the devices as well as a plurality of slidable catheters within to aid in delivery and or placement. When in the delivery catheter, each fixation element is compressed to a substantially cylindrical tubular structure. The distal end of the delivery catheter is introduced into the desired target site, such as a bronchi, and the first fixation element is released from the delivery catheter. Since the fixation element is self-expanding, the expandable central region of the fixation element expands radially outward, where it is held in place by the surrounding tissue into which it is implanted. This type of securement differs greatly from devices which engage the tissue by means of piercing elements. In addition, it differs from other devices that expand at the ends of the structure. The use of a radially expanding central region allows for quick and easy removal of the fixation element after it is deployed if desired. Further, the use of a fixation element having multiple expandable central regions (such as in FIG. 5) allows for easier placement and accuracy in alignment of delivery. This configuration also may minimize tissue or airway trauma as the force can be distributed.

Once the first fixation element is deployed, the tissue can be pulled proximally (toward the user) to a desired length. In the case of lung volume reduction, this would entail deploying the first fixation element in the desired bronchial airway and pulling that region of the lung a desired length. Once the tissue is pulled to a desired length, the second fixation element may be deployed into tissue and secured into place via a locking feature (for example, 695 or 760 above), such as a tang (830) described above. Prior to deploying the locking feature, a feature in the assembly may be used to temporarily hold tension on the tether such that the clinician can assess and possibly adjust additional tethers before securing the implanted device. If multiple distal fixation elements are used, each would be deployed in the desired locations prior to deployment of the second (proximal) fixation element. Once the locking feature is deployed, the tether(s) may be severed and the delivery catheter can be removed.

In some embodiments, the first fixation element may be deployed in a desired location, followed by deployment of the second fixation element in a desired location, and then followed by pulling of the tether, such that the first fixation element moves in a proximal fashion towards the deployed second fixation element. When the desired pulling has been achieved, the locking mechanism may be deployed to maintain the second fixation element in the desired location and tether length. Alternatively, the device may be deployed by releasing the first fixation element, followed by pulling the tether such that the first fixation element is pulled to a desired length, and then releasing the second fixation element and locking the second fixation element in place. In still other aspects, the first and second fixation elements may be deployed at their respective locations, and a one-way locking mechanism may be used to hold the second fixation element in place. A one-way locking mechanism may restrict the second fixation element from moving along the tether in a distal direction (e.g., towards the first fixation element), but may allow a user to pull the tether through the second fixation element in a proximal direction, thus pulling the first fixation element towards the second fixation element after locking.

The size, shape and wall thickness as well as the pre-shaping of the fixation elements will determine their respective shape once deployed. The locking feature may be controllably releasable by either a physical or remote device. In some embodiments, the tether/tethers may be notched or barbed as to control or limit the movement between a distal and proximal fixed point, and the use of physical notches or barbs may provide a tactile or sensory feedback to the user during deployment. Multiple first (distal) fixation elements may be deployed and be individually or simultaneously pulled until the desired length, and then locked onto the second (proximal) fixation element, either individually locked or locked as a group.

The use of fixation elements that have an open structure, such as that described above through the use of slits and struts provides additional benefits, such as allowing fluid drainage. However, the fixation elements may be solid in design, or be hollow and contain a membrane and could be made of any material compatible to the body. The locking of the device may be achieved with such devices as clips, tension, serpentine loops, slip knots or any means to lock and maintain tension. The material used to be used as an fixation element or to secure the device may be made of a breathable or non-breathable material. The fixation elements and/or tether may be used in combination with gels containing other properties and/or drugs.

The tether or tethers used may be monofilament or multifilament, or may be braided or unbraided. It is desired, however, that the tethers be unbraided so as to reduce attracting ingrowth or bacteria. The tether and/or fixation elements may also be sheathed to aid in deployment or positioning.

The fixation elements may be surface treated so as to aid in gripping and holding strength of the fixation element once deployed. Increased gripping of the fixation element may also come as part of the design; either by pre-shape or cut design made by a laser (or other cutting device or method) in a Nitinol fixation element. Although a smooth outer surface is useful in the present invention and may provide a less traumatic device, some degree of surface roughening or gripping elements are preferred so as to avoid slippage in the airway when under tension. Therefore surface roughness instead of surface polishing may be employed. This may or may not be combined with physical points or protrusions or sections of the expandable fixation element which only become exposed once the device is deployed and the central region of the fixation element is radially extended. For example, physical points or protrusions may have a sharp surface, or may have a broader surface, or may have a higher surface area or other features that increase holding strength of the fixation element. In one embodiment, the fixation element may include a barb or other gripping element. By exposed it is meant that the protrusion has a diameter or measurement which is greater that the diameter or measurement of the surface adjacent to the protrusion.

The tethered fixation elements could be placed blindly or under visualization, where any of the fixation elements and/or the tether (including termination feature and/or locking feature) includes visualization elements, such as radiopaque markers, fluorescence, or other elements that can be seen by a user during implantation in the body cavity. The use of such visualization elements or makers not only assist in fixation element placement, but also provide the user with an improvement means of determining the degree of tissue retraction/movement achieved or desired. Additionally, the fixation elements and/or tether may contain or be coated with a drug or chemical to aid or treat surrounding tissue, such as an anti-microbial agent or other composition.

One or more fixation element can be deployed from one or more catheters, which may reside within one another, which may or may not be delivered via a bronchial scope to the targeted lung area. It is desired to deliver them under visualization of the human eye, but for some very distal fixation element placements that may not be possible due to the size of the airway being targeted. For very small airways or for patients who cannot undergo a large bronchial scope blocking their airway during treatment, placement of devices may be accomplished through electronic or computer guided visualization of small catheters to the targeted location.

FIGS. 9-13 depict various configurations useful as fixation elements, devices, and deployment devices. The descriptions of the device and the fixation elements, including materials, sizes, and deployment methods apply to FIGS. 9-13. As can be seen, device assembly 1000 includes the implantable device 1010, with first fixation element 1030 and second fixation element 1050 secured to a tether 1040. Fixation elements 1030 and 1050 may be slidably secured to the tether 1040 as described above. First fixation element 1030 is held securely on the tether 1040 by termination feature 1020 at the distal end of the tether 1040. The assembly 1000 includes a catheter 1060 or other deployment device, which is used to deploy the implantable device 1010.

Figure 10:
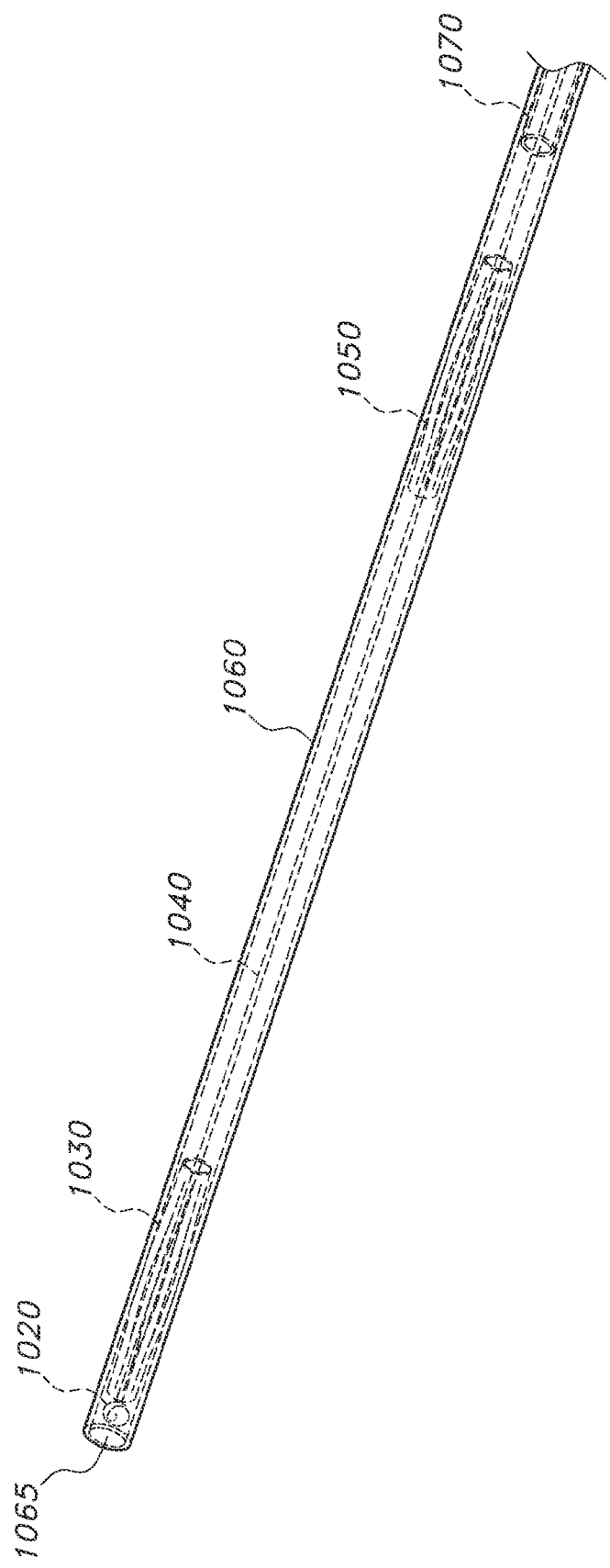
FIG. 10 shows deployment of a device in a collapsed state and in a delivery device.
Figure 13B:
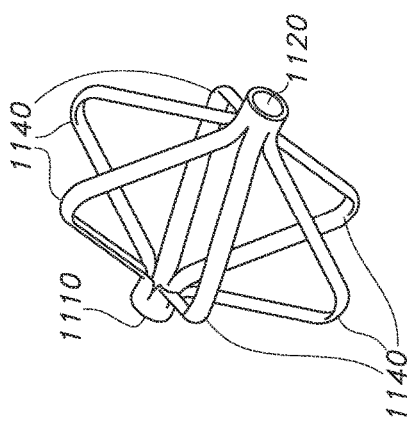
FIGS. 13A-13D show variations of configurations of the fixation elements useful herein.
Figure 13D:
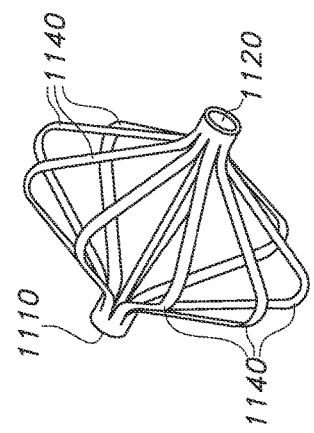
Figure 13A:
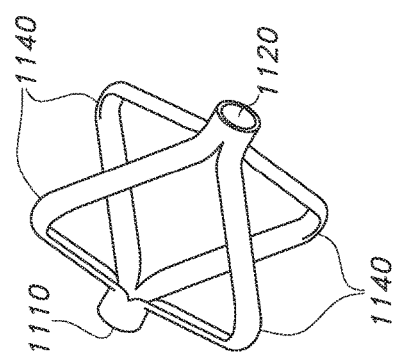
Figure 13C:
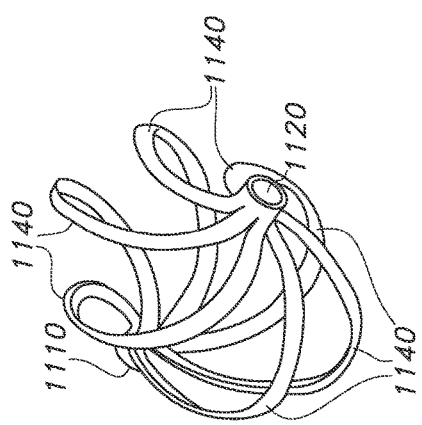

FIG. 10 shows the implantable device 1010 held within the deployment device or catheter 1060. As can be seen, first fixation element 1030 and second fixation element 1050 are in the compressed configuration, since they are held against the sidewalls of the catheter 1060. At the distal end of catheter 1060 is an open aperture or delivery port 1065, through which the implantable device 1010 can be delivered. Catheter 1060 may include any delivery device, such as a pusher 1070, to effectuate delivery of the device 1010 when desired. It can be envisioned that fixation elements 1030 and 1050 may or may not be located together in the delivery device.

FIGS. 11-13 show various configurations of fixation elements that are useful in the device. FIGS. 11A-11C show a representative fixation element 1100 in a compressed configuration, as it would be while within a delivery device, while FIGS. 12A-12C show the same fixation element 1100 in an expanded state, as it would be after deployment at the target site. The fixation element 1100 includes a first end 1110 and second end 1120, as described above, which may be open ends, through which a tether or other elongated device may be passed through. Fixation element 1100 includes a plurality of axially elongated slits or windows 1130 arranged about the circumference of the fixation element 1100. Presence of slits 1130 creates a plurality of struts 1140, which are formed by the cutting of slits 1130 in the fixation element 1100. FIG. 11A shows a side view of the compressed fixation element, FIG. 11B shows an axial view of the compressed fixation element 1100, while FIG. 11C shows a perspective view of the compressed fixation element 1100.

After the fixation element 1100 is released from its compressed state, such as after deployment through a catheter or other deployment device, it takes the expanded state, which can be seen in FIG. 12. As seen, in this exemplary Figure, the fixation element 1100 includes the same first end 1110, second end 1120, and plurality of slits 1130 forming struts 1140. However, the struts 1140 have been treated to have shape memory, and in the absence of force thereon, the struts 1140 expand to their desired shape, which is a radial expansion. FIG. 12A shows a side view of the expanded fixation element, FIG. 12B shows an axial view of the expanded fixation element 1100, while FIG. 12C shows a perspective view of the expanded fixation element 1100.

FIGS. 13A-13D show various configurations of expanded fixation elements 1100 that may be useful in the implantable device. For example, the fixation element 1100 may include axially aligned four struts 1140 (FIG. 13A), it may include axially aligned six struts (FIG. 13B), it may include a twisted configuration (FIG. 13C), it may include nine axially aligned struts (FIG. 13D), or various combinations thereof. Any number of struts may be used, and they may be arranged axially aligned as in FIGS. 13A, 13B, and 13D, or they may be twisted or helically aligned as in FIG. 13C. They may be angled, shaped, have differing cross-sectional configurations, be made from differing materials, and the like. Other similar configurations or number of struts 1140 may be used.

Various fixation element prototypes were prepared and tested to determine chronic outward force (COF), and to show general examples of fixation devices useful in the present invention. The fixation elements were tubular devices including a plurality of slits to form axial struts. Five samples were tested, samples S1-S4 had an inner diameter of about 0.0375 inches and sample S5 had an inner diameter of about 0.0245 inches. Force values were tested at 2.5 mm and at 3.0 mm (expanded diameter), and each sample was tested two times. The data provided at 2.5 and 3.0 mm is directional, and it would be known to test sizes both larger and smaller where appropriate. The testing was conducted on an RX600, an MSI Radial expansion Force Gauge Tester. The testing was conducted at approximately 37.5 degrees C. (approximately body temperature). The average force values generated (N-Hoop force), after two tests on each product, are summarized in the tables below. The data provided is Hoop force (Newtons), and one of ordinary skill in the art could convert to radial force if desired.

TABLE

Chronic Outward Force (in N) of Five Samples

| | S1 (0.0375 inch ID) | S2 (0.0375 inch ID) | S3 (0.0375 inch ID) | S4 (0.0375 inch ID) | S5 (0.0245 inch ID) |
|---|---|---|---|---|---|
| COF = 2.5 mm | 0.525 N | 0.975 N | 0.64 N | 0.67 N | 0.295 N |
| COF = 3.0 mm | 0.485 N | 0.805 N | 0.58 N | 0.525 N | 0.105 N |

As can be seen, the four samples having an inner diameter of about 0.0375 inches demonstrated a COF of about 0.525 N to about 0.975 N (at 2.5 mm), and a COF of about 0.485 N to about 0.805 N (at 3.0 mm). If sample 2 is removed, the ranges are COF (at 2.5 mm) from 0.525 N to 0.67 N and COF (at 3.0 mm) from 0.485 N to 0.58 N. It is noted that Sample 5 demonstrated smaller COF numbers, presumably due to the smaller diameter of the sample fixation element.

Variation in hoop-force can be due to variations experienced by electro polishing or thinning of the struts. The hoop force will vary with design changes to the shape, configuration, material, wall thickness and length of the radially expanding fixation elements, which can also be seen in the data as a static design begins to expand. Another factor that changes expansion is temperature at which the expanding fixation elements are set, and the fixture setting. It may be set at an austenitic setting (higher temperature phase, stronger) or martensitic (lower temperature phase, less strong).

One can also imagine that unique force profile gradients exist between the fully compressed state and the fully expanded state. This profile may or may not be linear and may be influenced by at least one if not multiple factors described herein.

What is claimed is:

1. A device for reducing the volume of a tissue region, the device comprising:
   (a) a first fixation element,
   (b) a second fixation element, and
   (c) a tethering device, wherein the tethering device includes an internal channel configured to permit the delivery of a substance therein,
   wherein said first and second fixation elements are slidably secured onto said tether such that at least one of the first and second fixation elements are configured to translate along the tether in a proximal direction and a distal direction in an unlocked configuration,
   wherein said first and second fixation elements are radially self-expanding fixation elements,
   wherein at least one of said first and second fixation elements comprises a tubular region at an end thereof,
   said tubular region comprising a cylindrical wall and a hollow opening therethrough configured to include a portion of said tether,
   said tubular region further comprising a tang formed into an opening defined through at least a portion of said cylindrical wall,
   wherein said tang has a generally claw or hook shape biased into said hollow opening and toward said tether inside said tubular region,
   said tang comprising an end integrated with or integrally formed with said sidewall and a depression end opposite thereof in contact with said tether in said hollow opening, and
   wherein said depression end comprises a series of teeth or protrusions configured to grip a portion of said tether to restrict movement of said tether in said tubular region.

2. The device of claim 1, wherein said first and second fixation elements comprise a shape memory material.

3. The device of claim 2, wherein said shape memory material is nitinol.

4. The device of claim 1, further comprising a tubular delivery device having an open interior into which said device may be held such that said first and second fixation elements are compressed within the open interior of said delivery device.

5. The device of claim 1, wherein at least one of said fixation elements can be compressed after being expanded.

6. The device of claim 1, further comprising a coating comprising an anti-microbial composition.

7. A method of achieving reduction of a volume of tissue, comprising:
   (i) guiding a distal end of a tubular delivery device having an open interior region into a first target site of a tissue, wherein said tubular delivery device comprises an implantable device within the open interior of the tubular delivery device, the implantable device comprising:
      (a) a first radially self-expanding fixation element;
      (b) a second radially self-expanding fixation element; and
      (c) a tethering device, wherein said first and second fixation elements are slidably secured onto said tether;
   (ii) releasing said first radially self-expanding fixation element from the open interior of the tubular delivery device, such that the first radially self-expanding fixation element expands and exerts a first radially outward force on the first target site of tissue;
   (iii) positioning said distal end of the tubular delivery device to a second target site within said tissue,
   (iv) releasing said second radially self-expanding fixation element from the open interior of the tubular delivery device, such that the second radially self-expanding fixation element expands and exerts a second radially outward force on the second target site of tissue;
   (v) pulling said tethering device such that the first radially self-expanding fixation element is pulled proximally towards the second fixation element to a desired length, wherein the first radially self-expanding fixation element proximally carries the first target site of tissue in response to being pulled proximally by the tethering device via the first radially outward force.

8. The method of claim 7, further comprising locking said second radially self-expanding fixation element after pulling said tethering device.

9. The method of claim 7, further comprising locking said second radially self-expanding fixation element prior to pulling said tethering device.

10. The method of claim 7, wherein each of said first and second fixation elements is generally shaped so as to fit into a delivery device in a compressed state, wherein each of said first and second fixation elements has a first end and a second end and an intervening body therebetween, and wherein each intervening body has a plurality of slits cut therein to provide a plurality of axially configured struts.

11. The method of claim 10, wherein said fixation elements are treated so as to be self-expanding in a radially outward direction.

12. The method of claim 11, wherein said fixation elements comprise a shape memory material.

13. The method of claim 12, wherein said fixation elements comprise nitinol.

14. The method of claim 7, wherein said first fixation element is locked to said tethering device using said tang in said tubular region so as to restrict said first fixation element from sliding along said tethering device.

15. The method of claim 7, further comprising compressing said first radially self-expanding fixation element after said step (ii) of releasing said first radially self-expanding fixation element.

16. The method of claim 15, further comprising allowing said first radially self-expanding fixation element to expand radially after said step of compressing said first radially self-expanding fixation element after said step (ii) of releasing said first radially self-expanding fixation element.

17. A device for reducing the volume of a tissue region, the device comprising:
   (a) a first fixation element;
   (b) a second fixation element; and
   (c) a tethering device, wherein the tethering device includes an internal channel configured to permit the delivery of a substance therein;
   wherein said first and second fixation elements are slidably translatable along the tether, wherein the first and second fixation elements are configured to expand radially outwardly,
   wherein at least one of the first and second fixation elements includes a tubular region, wherein the tubular region includes a cylindrical wall and a hollow opening therethrough, wherein the hollow opening is configured to slidably receive the tether;
   wherein the tubular region further includes a lock abutting against the tether within the hollow opening, wherein the lock is configured to be actuated between an unlocked state and a locked state; and
   wherein the lock is configured to allow slidable translation of the tether relative to the first and second fixational elements when in the unlocked state, wherein the lock is configured to inhibit slidable translation of the tether relative to the first and second fixational elements when in the locked state.

18. The device of claim 17, wherein the lock comprises a series of teeth or protrusions configured to engage the tether.

19. The device of claim 17, wherein the lock comprises a wedge configured to engage the tether.

20. The device of claim 17, wherein the tether includes a braided or multifilament surface configured to engage the corresponding lock when in the locked state.

* * * * *